(12) United States Patent
Numata et al.

(10) Patent No.: US 8,757,383 B2
(45) Date of Patent: Jun. 24, 2014

(54) MEDICAL TRAY

(75) Inventors: Shigeki Numata, Fujinomiya (JP);
Fumio Yamamoto, Fujinomiya (JP);
Toshihiko Asao, Fujinomiya (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 0 days.

(21) Appl. No.: 13/601,580

(22) Filed: Aug. 31, 2012

(65) Prior Publication Data

US 2013/0056387 A1    Mar. 7, 2013

Related U.S. Application Data

(63) Continuation of application No. PCT/JP2011/050645, filed on Jan. 17, 2011.

(30) Foreign Application Priority Data

Mar. 5, 2010   (JP) .................................. 2010-049069

(51) Int. Cl.
*B65D 6/04*   (2006.01)
(52) U.S. Cl.
USPC ............ 206/557; 206/363; 206/438; 206/570
(58) Field of Classification Search
USPC .......... 206/557, 363–370, 438, 570–572, 564
See application file for complete search history.

(56) References Cited

U.S. PATENT DOCUMENTS

| 4,585,450 | A | * | 4/1986 | Rosch et al. | 604/390 |
|---|---|---|---|---|---|
| 4,886,165 | A | * | 12/1989 | Annett | 206/370 |
| 4,944,427 | A | * | 7/1990 | Yamada et al. | 220/495.01 |
| 5,031,768 | A | * | 7/1991 | Fischer | 206/370 |
| 5,615,639 | A | * | 4/1997 | Knight | 119/168 |
| 6,012,586 | A | * | 1/2000 | Misra | 206/571 |
| 6,540,078 | B1 | * | 4/2003 | Homent et al. | 206/438 |
| 2010/0095899 | A1 | * | 4/2010 | Lipscomb et al. | 119/167 |

FOREIGN PATENT DOCUMENTS

| JP | 8-207923 A | 8/1996 |
|---|---|---|
| JP | 3060031 B1 | 7/2000 |
| JP | 2002-029567 A | 1/2002 |
| JP | 2007-075511 A | 3/2007 |

OTHER PUBLICATIONS

International Search Report (PCT/ISA/210) issued on Feb. 8, 2011, by the Japanese Patent Office as the International Searching Authority for International Application No. PCT/JP2011/050645.

* cited by examiner

*Primary Examiner* — Anthony Stashick
*Assistant Examiner* — Ernesto Grano
(74) *Attorney, Agent, or Firm* — Buchanan Ingersoll & Rooney PC

(57) ABSTRACT

To provide a medical tray which can be made more compact upon discarding, the medical tray has a bottom portion, a side wall provided along an outer periphery of the bottom portion, and a pair of side wall deformation guiding portions provided at opposing positions of the side wall for guiding the side wall when the side wall is deformed into a convex state toward the bottom portion.

18 Claims, 12 Drawing Sheets

MEDICAL TRAY

CROSS REFERENCES TO RELATED APPLICATIONS

The disclosure here is based on the subject matter described in Japanese Patent Application No. 2010-049069 filed in the Japanese Patent Office on Mar. 5, 2010, the entire content of which is incorporated herein by reference.

TECHNICAL FIELD

The invention disclosed here generally pertains to a medical tray. More specifically, the invention involves a medical tray configured to hold medical devices and the like.

BACKGROUND DISCUSSION

In medical diagnosis, medical testing and medical treatment involving the use of catheters, necessary medical devices such as a catheter and a guide wire, drug and so forth are set on a medical tray and then taken out, upon treatment, from within the medical tray and used. After the treatment, the medical tray is no longer necessary and is thus discarded into the trash.

The volume of a trash used in a medical field is determined to some extent based on the shape of the inlet of an incineration system, and the cost required for disposing such trash is in most cases determined in a unit of trash. Therefore, it is desirable to make the medical tray as compact as possible so that a greater number of medical trays can be placed into the trash. Japanese Patent Laid-Open No. 2007-75511 is an example of a medical tray that can be made more compact upon disposal by folding the same such that a side wall is overlapped with a bottom face.

However, since a medical tray is generally configured such that a bottom portion thereof is wider than a side wall thereof and the area ratio of the bottom portion occupying in the overall medical tray is high, only if the side wall is folded, the medical tray is liable to be bulky in a trash like the medical tray disclosed in Patent Document 1.

SUMMARY

The medical tray disclosed here is configured to be made more compact for purposes of facilitating disposal.

A medical tray includes a bottom portion, a side wall provided along an outer periphery of the bottom portion, and a pair of side wall deformation guiding portions provided at opposing positions of the side wall for guiding the side wall when the side wall is deformed into a convex state toward the bottom portion.

Since the medical tray has the side wall deformation guiding portions, when the side wall is deformed into a convex shape toward the bottom portion to fold the bottom portion, force is likely to be applied locally to the bottom portion, and the bottom portion can be folded readily and the medical tray can be made more compact.

Each of the side wall deformation guiding portions preferably includes at least one of a constricted portion formed such that the width of the bottom portion is decreased to the inner side, a side wall grooved portion extending from an upper end of the side wall toward the bottom portion and formed by being recessed to the inner side of the side wall, a side wall upper end recessed portion formed from an upper end of the side wall recessed toward the bottom portion or a side wall upper end stepped portion formed from an upper end of the side wall formed in a stepped state toward the bottom portion, and a flange groove portion formed from a flange formed at an upper end of the side wall and recessed to the inner side of the side all. This helps facilitate local bending and deformation of the side wall.

Providing the medical tray with a folding guiding portion provided on the bottom portion between the paired side wall deformation guiding portions for guiding the folding of the bottom portion, allows the bottom portion to be bent at or in the proximity of a line interconnecting the paired side wall deformation guiding portions, and the bottom portion can be folded readily in a desired direction.

The folding guiding portion can include at least one of a rib or a notch formed on the bottom portion between the paired side wall deformation guiding portions and a bottom edge recessed portion formed from an edge of the bottom portion recessed in a face direction or a bottom edge stepped portion formed from an edge of the bottom portion formed in a stepped state in a face direction. Bending at a place displaced from a line interconnecting the paired side wall deformation guiding portions or from a portion in the proximity of the line is thus restricted. Since the bottom portion becomes relatively fragile at or in the proximity of the line, the bottom portion is bent at or in the proximity of the line interconnecting the paired side wall deformation guiding portions and the bottom portion can be folded readily in a desired direction.

When the bottom portion is folded, one of the opposing portions of the side wall which oppose each other is placed inside the other of the opposing portions so that one of the opposing portions of the folded medical tray divided into the two portions is accommodated in the other portion, and so the medical tray becomes more compact.

Dividing the bottom portion into two portions by a line interconnecting the paired side wall deformation guiding portions, the portion of the bottom portion on one end side is sized such that the portion is accommodated in the inside of the portion on the other end side. When the medical tray is folded, the one end side of the folded medical tray divided into the two portions is accommodated in the other end side, and the medical tray becomes more compact.

If, where the bottom portion is divided into two portions by a line interconnecting the paired side wall deformation guiding portions, the portion of the bottom portion on one end side is rounded at corners thereof rather than the portion on the other end side, then the one end side of the medical tray becomes further liable to be accommodated in the other end side.

The medical tray can also include a folding keeping portion for keeping the folded condition of the bottom portion, and so the folded medical tray is less likely to expand into an original state as it can be kept in the relatively compact state.

DETAILED DESCRIPTION

Figure 1:
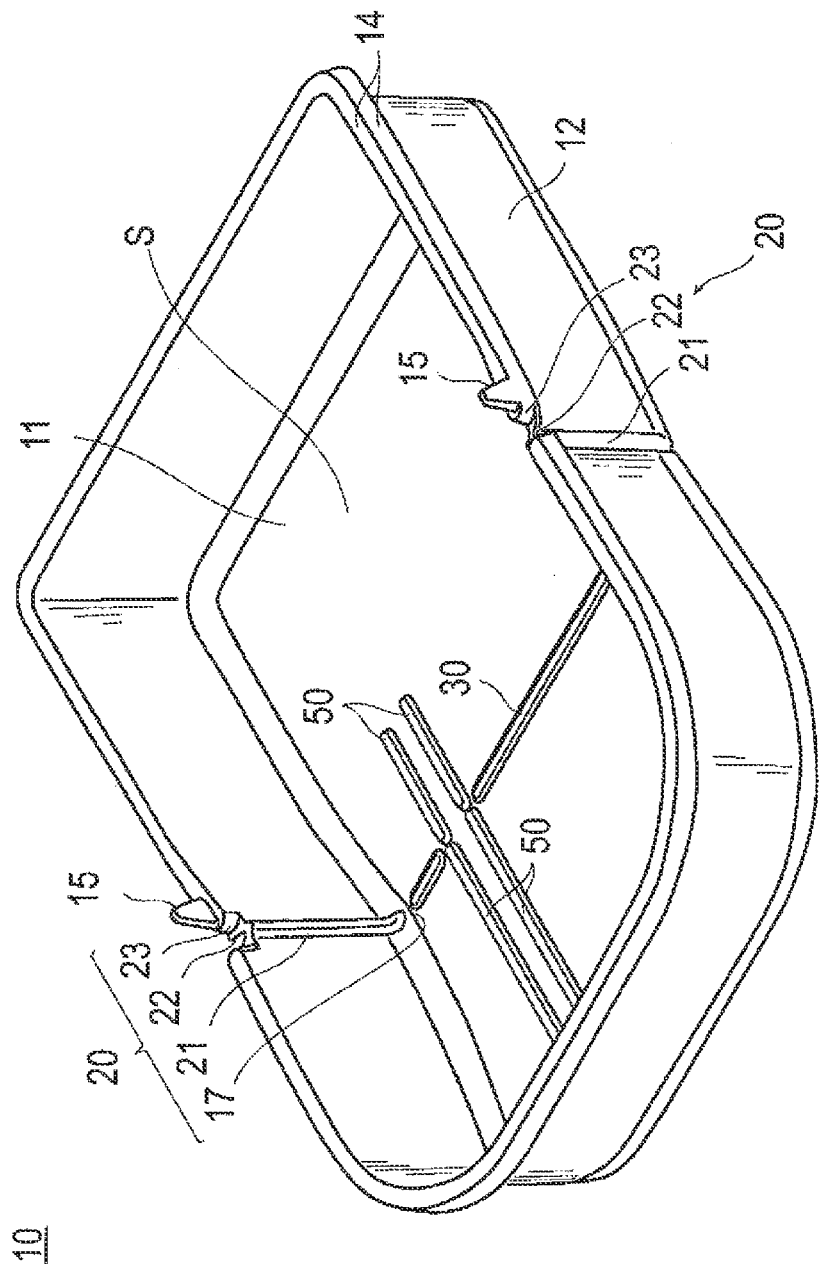
FIG. 1 is a perspective view of a medical tray according to an embodiment disclosed here by way of example.

Set forth below is a detailed description of the medical tray disclosed here. The medical tray illustrated and described represents an example of the medical tray disclosed here. For convenience and to help facilitate an understanding of the disclosure here, relative dimensions of features shown in the drawings are sometimes exaggerated and differ from actual ratios.

As shown in FIG. 1, a medical tray 10 according to the present embodiment includes a bottom portion 11, an upstanding side wall 12 extending along the outer periphery of the bottom portion 11, and a laterally outwardly directed flange 14 at the upper end of the side wall 12. Further, the medical tray 10 includes a pair of side wall deformation guiding portions 20 at opposing positions of the side wall 12, and a rib 30 (folding guiding portion) on the bottom portion 11 between the paired side wall deformation guiding portions 20 for guiding the bottom portion 11 upon folding.

The medical tray 10 is made of resin, has a relatively thin wall, and is vacuum formed from a thermoplastic resin sheet of, for example, polyethylene, polypropylene, polystyrene or polyvinylchloride. The bottom portion 11, side wall 12, flange 14, side wall deformation guiding portions 20 and rib 30 are formed integrally in one piece as a unitary structure.

The medical tray 10 has an accommodating space S formed from the bottom portion 11 and the side wall 12, and the accommodating space S is used to keep or hold medical devices and the like such as catheters, drugs and so forth which can be used during diagnosis, testing and medical treatment. Further, the medical tray 10 can be used also as a packaging tray for packaging a medical device(s), a drug(s) or the like. In this regard, the medical device(s), drug(s) and so forth are accommodated in the medical tray 10, the medical tray 10 containing the medical device(s), drug(s) and so forth is placed in a packaging bag, the packaging bag containing the medical tray 10 with the medical device(s), drug(s) and so forth is sealed, and the sealed bag is sterilized. The medical tray 10 and the medical device(s), drug(s) and so forth are thus sterilized for medical use.

Figure 2:
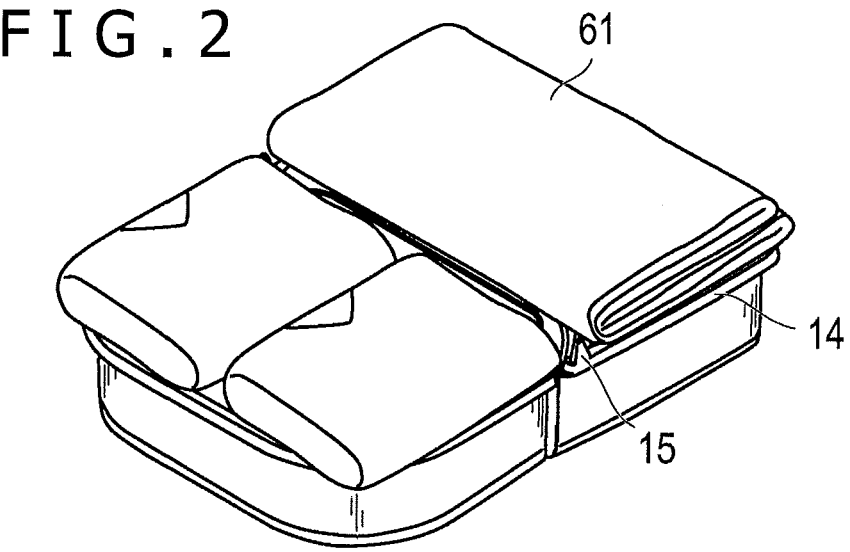
FIG. 2 is a perspective view of the medical tray showing examples of medical devices and the like disposed on the medical tray.
Figure 3:
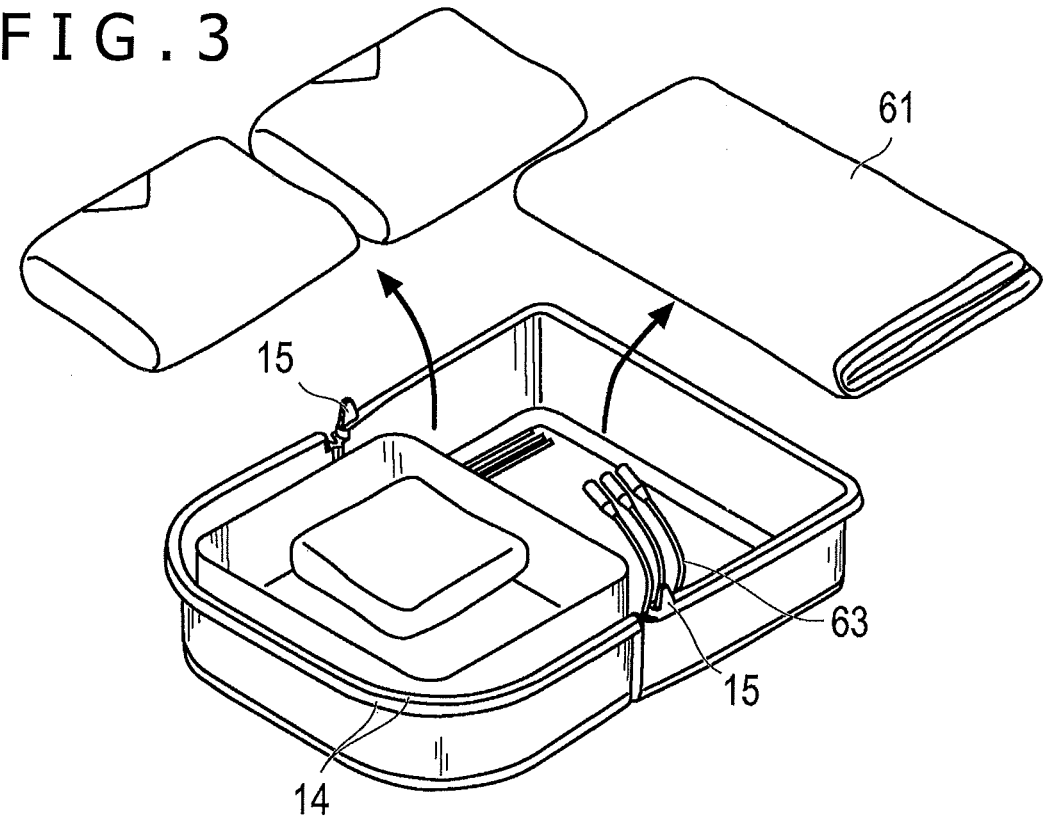
FIG. 3 is a perspective view of the medical tray illustrating the medical devices and the like taken out of the medical tray.

Then, as shown in FIGS. 2 and 3, upon carrying out diagnosis, testing and medical treatment, the packaging bag is opened to access the medical instruments, drugs and so forth located in the bag and set in the medical tray 10. Examples of medical devices include, in addition to catheters 63 and a drape 61, cotton swabs, syringes, guide wires, sheaths, dilators, scissors, tweezers and so forth. The drape 61 is placed on the medical tray 10 and positioned by projections 15 formed on the flange 14.

When treatment is to be carried out, a medical device is taken out from the medical tray 10, or during treatment, a medical device is placed into the medical tray 10 so that it is temporarily stored. Then, after the treatment, any medical device which is not needed any more is placed in the medical tray 10 and discarded together with the medical tray 10.

Figure 4:
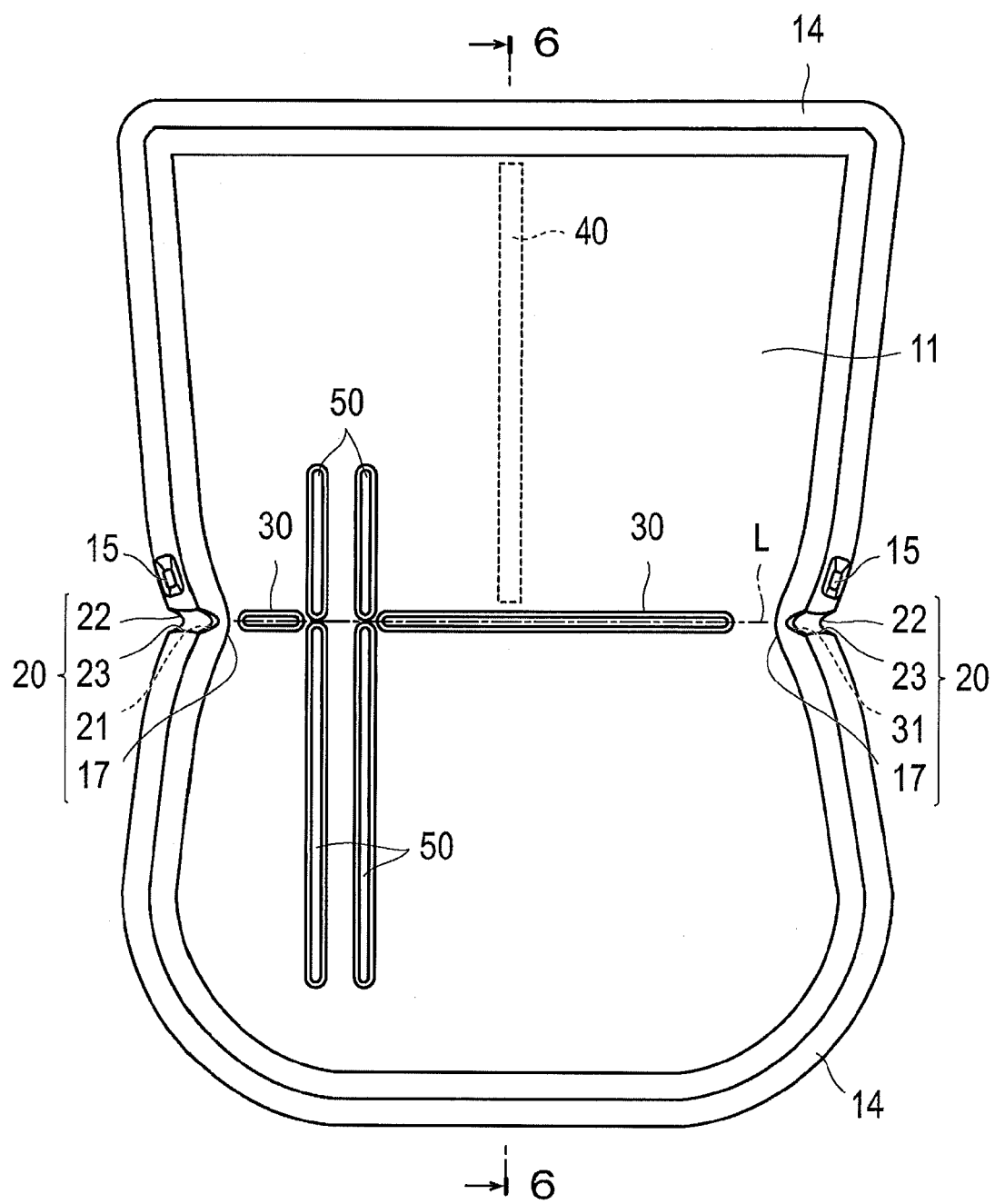
FIG. 4 is a plan view of the medical tray.

As shown in FIG. 4, the bottom portion 11 of the medical tray includes constricted portions (reduced width portions) 17 at which the width of the medical tray (internal dimension of the bottom portion) in the proximity of a substantially central portion (in the proximity of a line L) is reduced in comparison with portions of the medical tray immediately adjoining the constricted portions on opposite ends or sides of the constricted portion. Since the bottom portion 11 has the constricted portions 17, the edge (outer edge) portions of the bottom portion 11 are moderately recessed toward side wall groove portions 21 provided in the proximity of a substantially middle portion of the side wall 12. Further, the bottom portion 11 has a substantially rectangular shape overall, with two longer sides and two shorter sides, and the constricted portions 17 are provided on the two longer sides. The side wall deformation guiding portions 20 are provided at positions displaced a little from the center of the respective long side of the bottom portion 11. The deformation guiding portions 20 are positioned so that the part (smaller portion) of the bottom portion 11 on one side (end) of the line (straight line) L interconnecting the paired side wall deformation guiding portions 20 is sized so that it can be accommodated inside the other part (larger portion) of the bottom portion 11 on the other side (end) of the line L. The smaller bottom portion part is also configured slightly differently than the larger bottom portion part in that the smaller bottom portion part possesses rounded corner regions rather than the straighter corner regions on the larger bottom portion part. The line L is thus offset from the center of the bottom portion 11 considered with reference to the lengthwise dimension of the bottom portion.

By virtue of the constricted portions 17 provided on the bottom portion 11, the internal distance between opposing portions of the side wall 12 at the line L and in the proximity of the line L is smaller than the distance between opposing portions of the side wall 12 at opposite ends of the medical tray.

The rib 30 projects toward the inner side of the medical tray 10 (toward the accommodating space S side) and extends like a ridge. The rib 30 is a line formed three-dimensionally on the bottom portion 11 and along the line L. The rib 30 extends upwardly from the immediately surrounding portions of the bottom portion 11. In addition to the rib 30, ridge-like portions 50 are provided on the bottom portion 11. The ridge-like portions 50 are formed three-dimensionally on the bottom portion 11. The ridge-like portions 50 project toward the inner side of the medical tray 10 (toward the accommodating space S side) and extend like ridges in order to restrict disposition of an accommodated medical device thereon and/or to provide strength. In the present embodiment, the medical tray 10 is configured so that the ridge-like portions 50 are positioned in a direction crossing (e.g., perpendicular to) the rib 30, with the ridge-like portions 50 crossing or intersecting the rib 30 in this manner. But the ridge-like portions 50 can also preferably be formed divisionally on the opposite sides of the rib 30 so that the ridge-like portions 50 stop short of the rib 30 and do not actually intersect the rib 30. In this way, the folding of the bottom portion 11 may not be obstructed. The bottom portion 11 of the medical tray also includes an elongated tape 40 (folding keeping portion) for keeping or maintaining a folded state after the bottom portion 11 is folded. The elongated tape 40 is positioned on the outer surface of the bottom portion 11.

Figure 5:
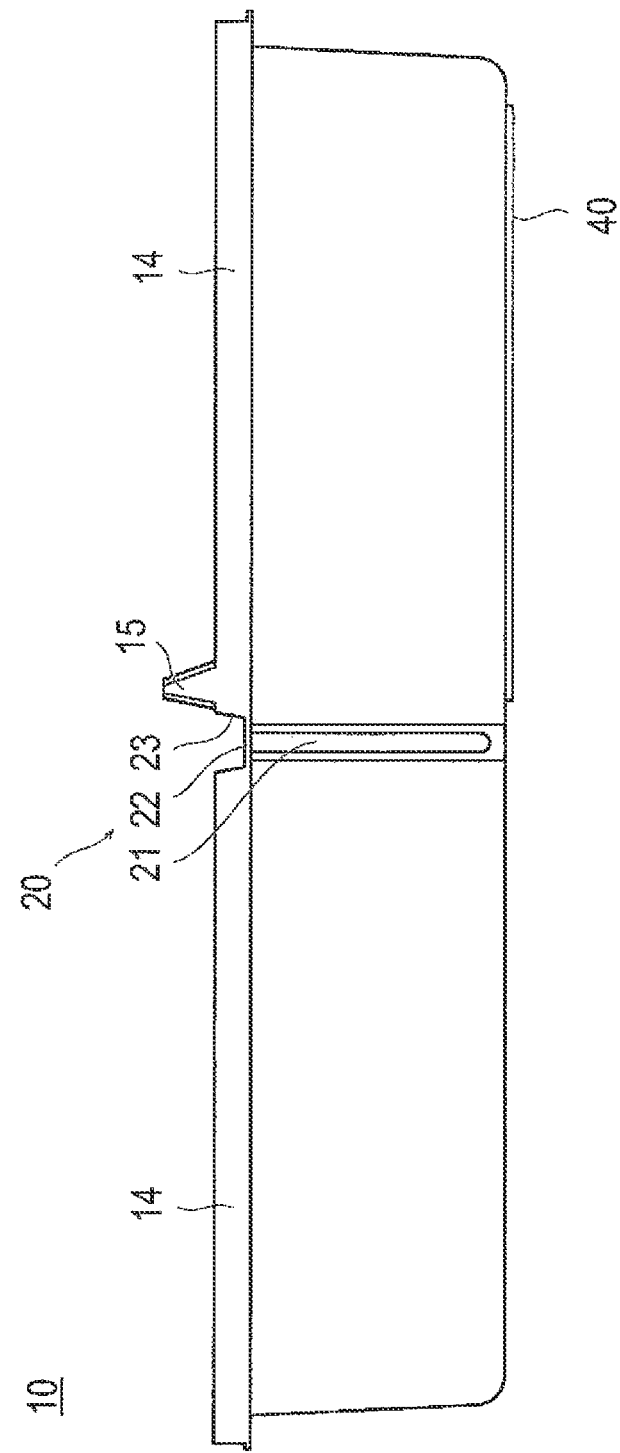
FIG. 5 is a side view of the medical tray.

As shown in FIGS. 4 and 5, the side wall deformation guiding portion 20 on each side wall 12 is configured from a combination of the constricted portion 17 (refer to FIG. 4) possessing an inner width at the bottom portion 11 that is reduced, a flange groove portion 22 (refer to FIG. 4) in which the flange 14 is recessed toward the inner side of the side wall 12, a side wall groove portion 21 (refer to FIG. 5) extending from the upper end of the side wall 12 toward the bottom portion 11 and recessed toward the inner side of the side wall 12, and a side wall upper end recessed portion 23 (refer to FIG. 5) formed such that an upper end of the side wall 12 is recessed toward the bottom portion 11.

Figure 6:
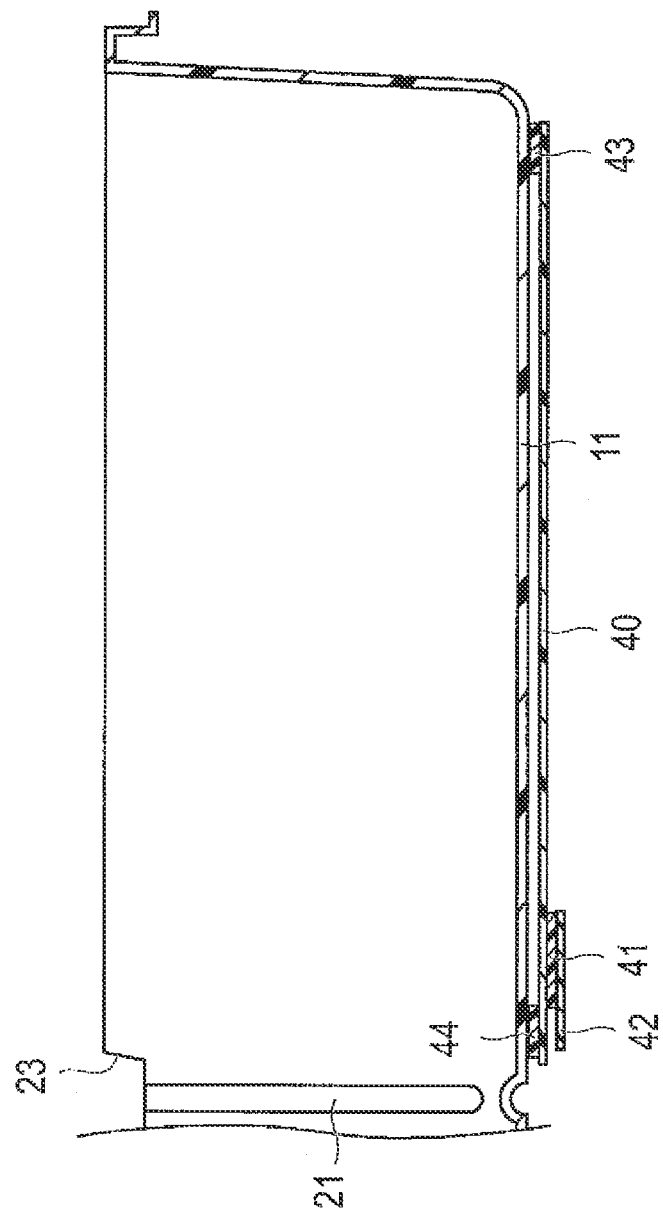
FIG. 6 is a partially enlarged cross-sectional view of the medical tray taken along the section line 6-6 of FIG. 4.

As shown in FIG. 6, the tape (folding keeping portion) 40 is adhered to the outside surface of the bottom portion 11 by adhesive. In the illustrated embodiment, the tape 40 is adhered to the outside surface of the bottom portion 11 by two adhesive pieces 43, 44 spaced apart from one another at the opposite ends of the tape 40. The tape 40 is secured at one of its ends by the adhesive piece 43 such that it cannot be separated from the bottom portion 11 and is temporarily fastened at its other end by the adhesive piece 44 such that the other end of the tape 40 can be separated from the bottom portion 11. The tape 40 also has an adhesive piece 41 on the surface opposite to the surface on which the adhesive piece 44 is disposed. The adhesive piece 41 is covered with a removable sheet 42 which prevents adhesion of the adhesive piece 41 until the sheet 42 is removed.

A method of folding the medical tray 10 will now be described with reference to FIGS. 7 and 8.

Generally speaking, an operator who carries out folding would push the side wall deformation guiding portions 20, or portions in the proximity of the side wall deformation guiding portions 20, to push down the side wall 12 toward the bottom portion 11 and then fold the bottom portion 11 so that the medical tray 10 is collapsed to substantially one-half the medical tray's original size. This pushing of the side wall 12 causes the side wall 12 to move both inwardly and downwardly as shown in FIG. 7.

Figure 7:
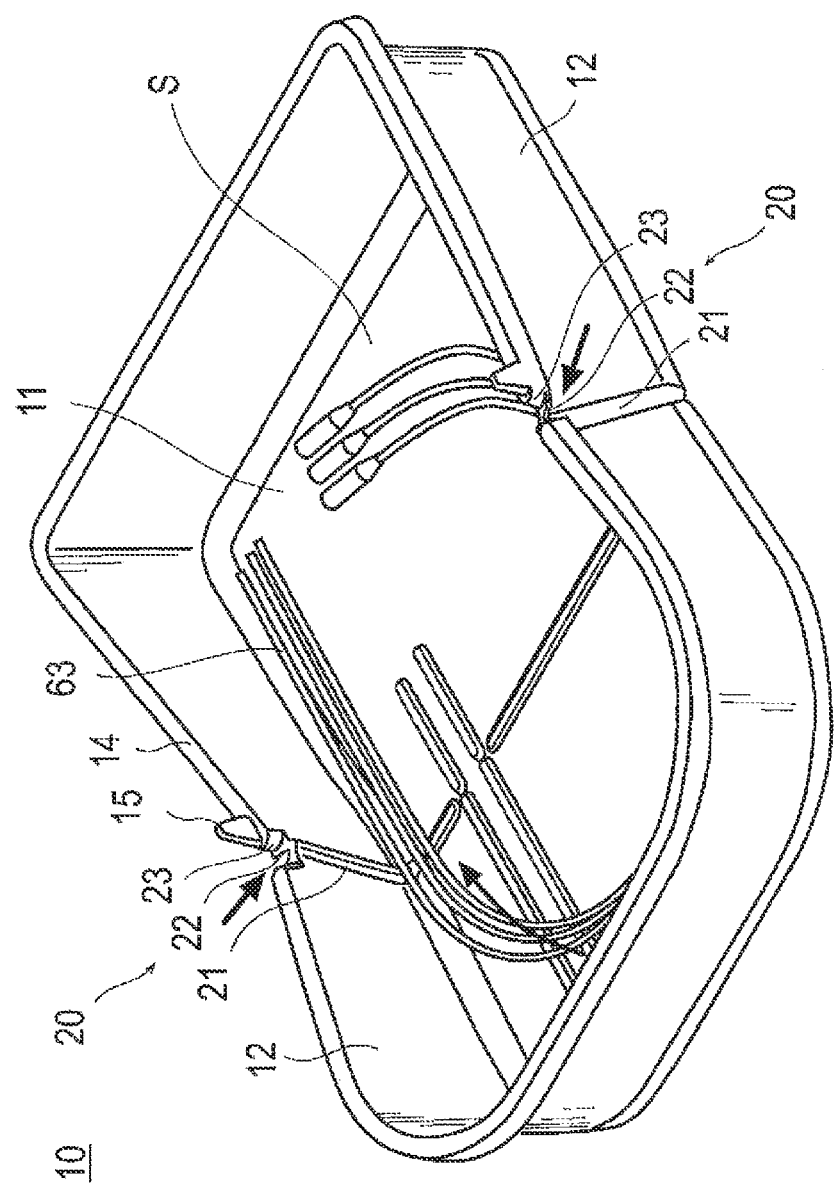
FIG. 7 is a perspective of the medical tray while being folded.

As shown in FIG. 7, for example, when the medical tray 10 is to be discarded together with medical devices such as the catheters 63 after they are used, by sandwiching and pressing the catheters 63 between and by the pushed down side wall 12 and the bottom portion 11, the catheters 63 can be prevented from undesirably jumping out of the medical tray by elastic force when the bottom portion 11 is collapsed.

Figure 8A:
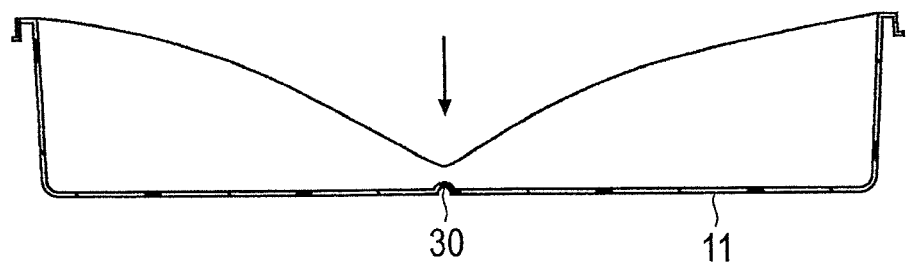
FIG. 8A is a cross-sectional view of the medical tray illustrating a state in which a side wall is pushed down toward a bottom portion during folding of the medical tray.
Figure 8B:
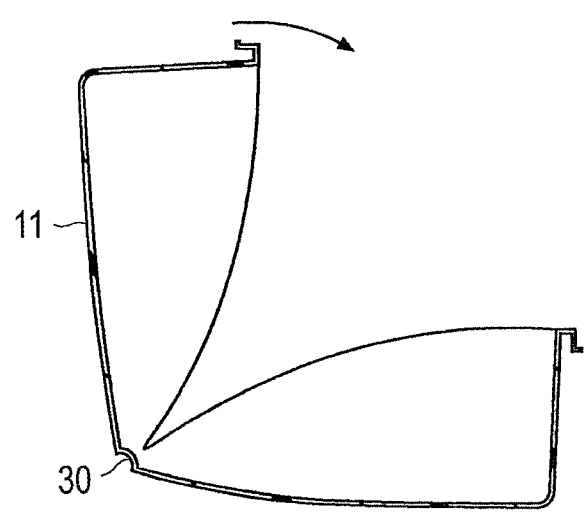
FIG. 8B is a cross-sectional view of the medical device illustrating a state in which the bottom portion of the medical tray is bent during folding of the medical tray.
Figure 8C:
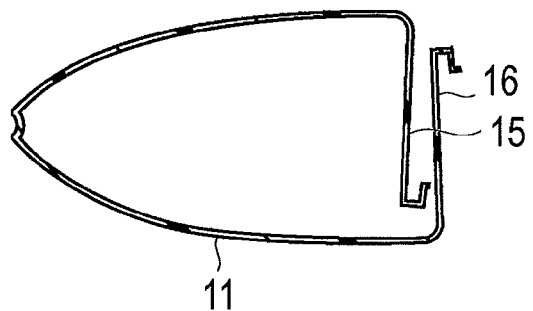
FIG. 8C is a cross-sectional view of the medical device illustrating a state in which one of the opposing facing portions of the side wall is pushed into the inner side of the other one of the facing portions during folding of the medical tray.

As shown in FIG. 8(A), the crushed side wall 12 is deformed at the side wall deformation guiding portions 20 or in the proximity of the side wall deformation guiding portions 20 into a convex form toward the bottom portion 11. Then, the bottom portion 11 is folded at or in the proximity of the rib 30 as shown in FIG. 8(B) or at or in the proximity of the line L, and one of the opposing surfaces 15 of the side wall 12 is placed inside the other opposing surface 16 as shown in FIG. 8(C).

Figure 9A:
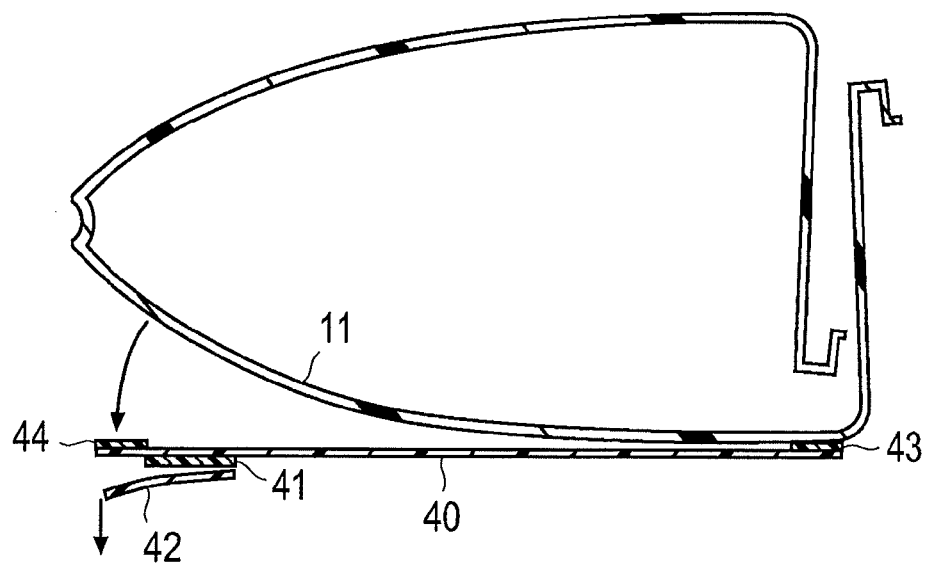
FIG. 9A is a cross-sectional view of the medical device illustrating a state in which one end of a tape temporarily fastened to the bottom portion of the medical tray is exfoliated or removed from the bottom portion after the medical tray is folded.
Figure 9B:
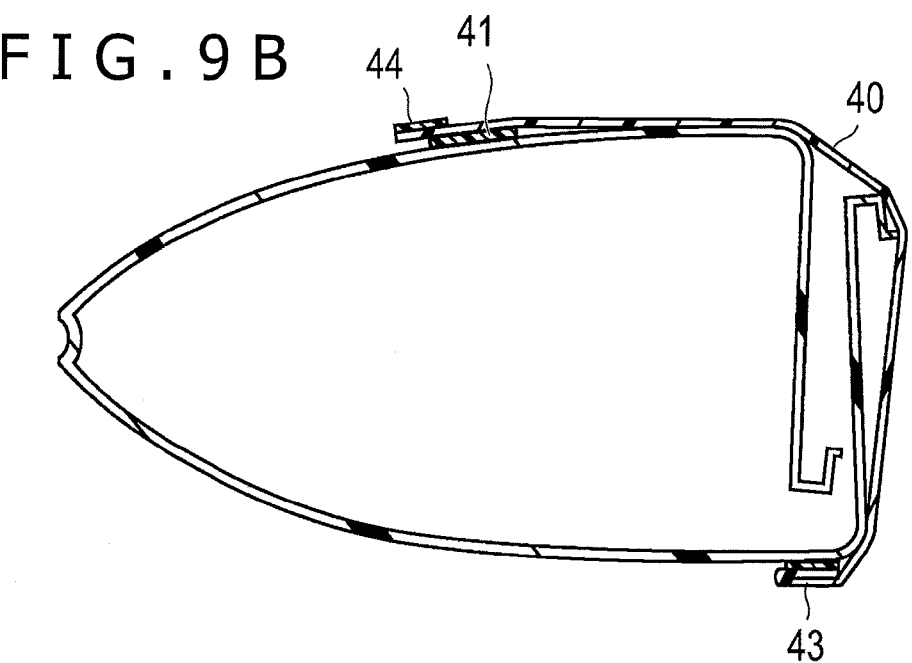
FIG. 9B is a cross-sectional view of the medical tray in the folded state, wherein the folded state is kept by a tape.

The operator next removes or separates the one end of the tape 40, temporarily fastened to the bottom portion 11 by the adhesive piece 44, from the bottom portion 11 and removes the sheet 42 covering the adhesive piece 41 as shown in FIG. 9(A). Thereafter, the exposed adhesive piece 41 at the one end of the tape 40 is adhered to one of the two divisional portions of the bottom portion 11 in the folded state so that the tape 40 keeps or maintains the folded state of the bottom portion 11 (medical tray) as shown in FIG. 9(B).

Figure 10:
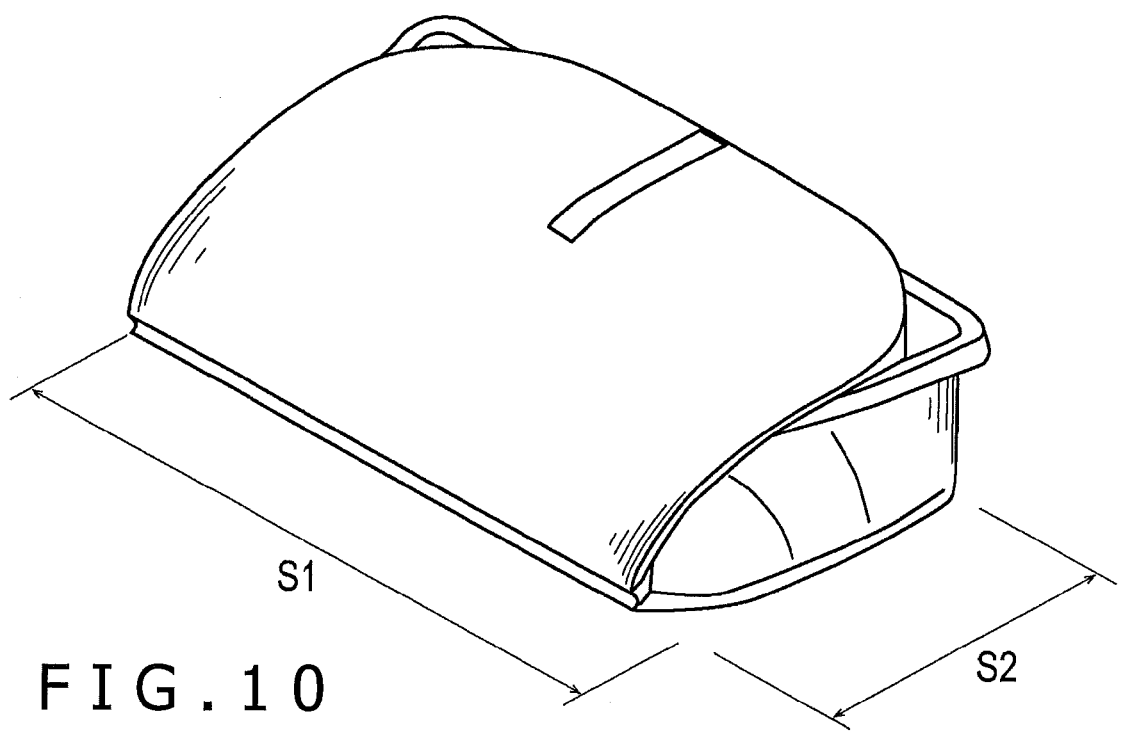
FIG. 10 is a perspective view of the medical tray after the medical tray is folded.

Thereafter, the medical tray 10 is discarded in a folded state into the trash as shown in FIG. 10. Although various dimensions of the medical tray 10 can be set suitably, the medical tray 10 preferably has a size with which the medical tray 10 in a folded state shown in FIG. 10 can be put as it is into a trash receptacle. Since the opening of trash receptacles used in the medical field frequently has a substantially rectangular shape, the dimension S1 in the longitudinal direction and the dimension S2 in the lateral direction of the bottom portion 11 (medical tray) after it is folded are smaller than the dimensions of the opening of the trash receptacle in the longitudinal direction and the lateral direction.

In the known medical tray described above, the medical tray is folded in such a manner that the face of the side wall overlaps with the bottom face, and the side wall is not deformed in a convex state toward the bottom portion. Rather, the side wall in the known medical tray is deformed in a direction substantially parallel to the face of the bottom face such that it is spaced away from the bottom portion, and the side wall and the bottom portion contact each other at the facing surfaces.

On the other hand, in the medical tray illustrated and described here as an example of the disclosed medical tray, the medical tray 10 has the side wall deformation guiding portions 20 and so the side wall 12 is deformed in a convex state toward the bottom portion 11. When the bottom portion 11 is folded, force is likely to be applied locally to the line L or to a portion in the proximity of the line L, and the bottom portion 11 is folded rather readily and the medical tray 10 to be discarded can be made more compact.

Each side wall deformation guiding portion 20 is configured from the constricted portions 17, the flange groove portion 22, the side wall groove portion 21 and the side wall upper end recessed portion 23. This contributes to the side wall 12 being bent locally and so the side wall 12 is more likely to be deformed as desired.

Since each side wall deformation guiding portion 20 in the medical tray 10 includes the flange groove portion 22, it is possible to provide the two conflicting functions of reinforcement of the medical tray 10 by the flange 14 and relative easiness of folding.

In the known medical tray described above, waste such as cotton swabs which are not needed any more are hidden by folding the side wall, and so the side wall must be relatively high. The medical tray thus becomes rather deep. Therefore, there is the possibility that the usability of the medical tray may be deteriorated when, for example, trying to remove a medical device.

On the other hand, with the medical tray disclosed here, waste matter is concealed by folding the bottom portion 11 and so the medical tray 10 is not subject to such a structural restriction. The height of the side wall can thus be relatively freely set. Thus, implementation of the medical tray 10 which is superior in usability can be achieved.

The rib 30 in the medical tray disclosed here restricts bending at a place displaced from the line L or from a portion near the line L. The bottom portion 11 is thus bent at or in the proximity of the line L and is liable to be folded in a desired direction.

The medical tray 10 is configured so that one of the two portions of the bottom portion 11 divided across the line L has a size with which it is accommodated in the inside of the other portion and, when the bottom portion 11 is folded, the one of the opposing face portions (surfaces) 15 of the side wall 12 which oppose each other is accommodated in the inside of the other face portion (surface) 16, and the one of the two divisional portions of the medical tray 10 in the folded state is accommodated in the other divisional portion so that the medical tray 10 becomes more compact.

The tape 40 helps maintain the folded configuration so that the medical tray 10 is less likely to be expanded to its original state and can keep the compact state.

The medical tray is not limited to the embodiment described above but can be modified in various manners.

Figure 11:
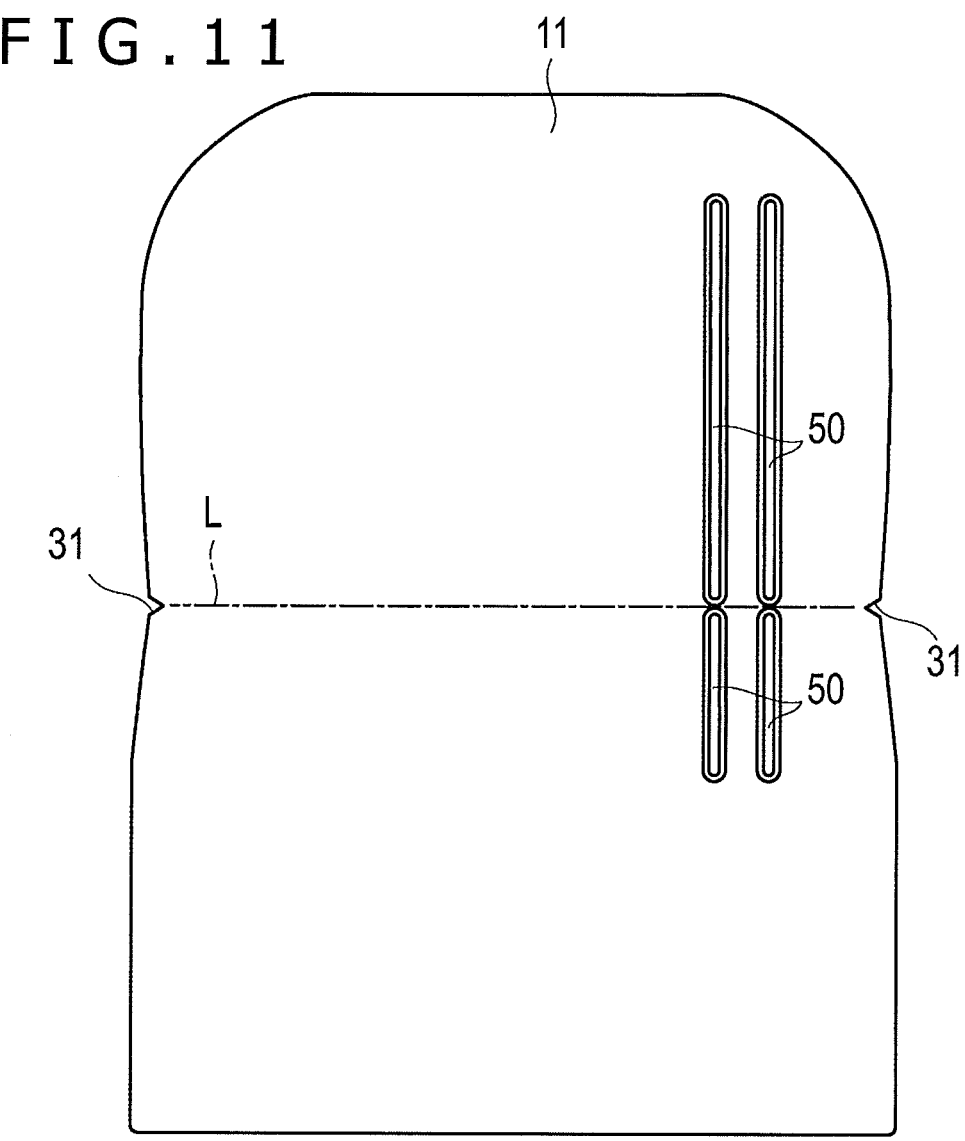
FIG. 11 is a plan view showing another example of a bottom portion of a medical tray according to the embodiment.
Figure 12:
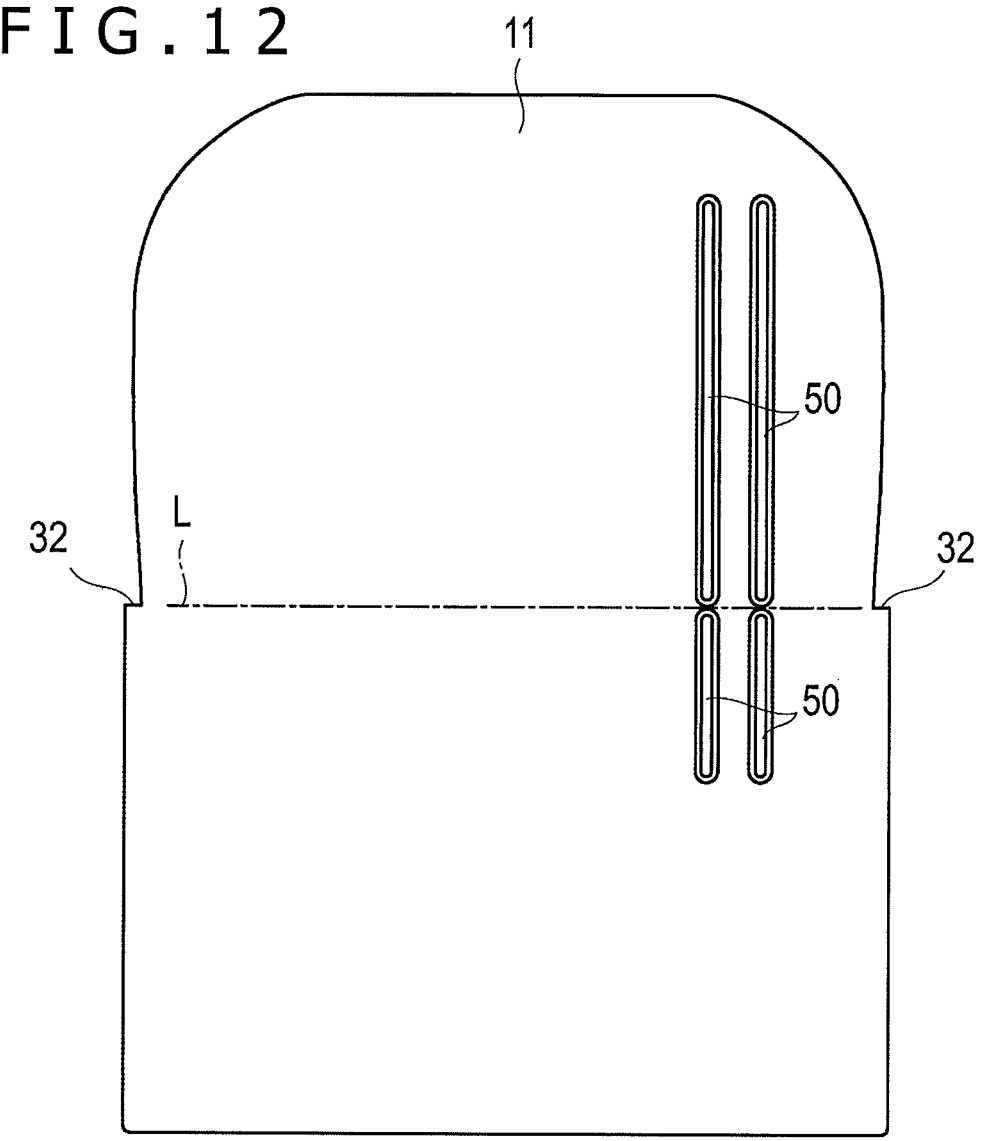
FIG. 12 is a plan view showing a further example of a bottom portion of a medical tray according to another embodiment.

For example, the folding guiding portion is not limited to the rib 30 but may be any element which is formed on the line L and decreases the bending rigidity. Thus, the folding guiding portion may be a notch (line which is formed three-dimensionally) formed such that only one surface is recessed in a concave state or may be a bottom edge recessed portion 31 formed such that an edge of the bottom portion 11 is recessed in a face direction or a bottom edge stepped portion 32 formed such that an edge of the bottom portion 11 is formed in a stepped state in a face direction as seen in FIG. 11 or 12. Or, the folding guiding portion may be configured from a combination of one of the rib 30 and a notch and one of the bottom edge recessed portion 31 and the bottom edge stepped portion 32.

The folding guiding portion is also not limited to a linear configuration such as the rib 30 in the embodiment described above, but may include a bent or curved portion. In other words, the line L interconnects a pair of side wall deformation guiding portions and may be not only a linear line but also a line having a bent or curved portion.

In the embodiment described above, the side wall deformation guiding portion is formed from the constricted portion 17, the flange groove portion 22, the side wall groove portion 21 and the side wall upper end recessed portion 23. But the side wall deformation guiding portion is not limited to this configuration and may be configured from only one of these portions or may be configured from two of them.

While the constricted portion 17 is shaped such that the width of the bottom portion 11 decreases to the inner side (inwardly) from one end toward a portion in the proximity of a substantially central portion and then increases to the outer side (outwardly) from the portion in the proximity of the substantially central portion toward the other end, it may be shaped otherwise such that the width of the bottom portion 11 gradually decreases to the inner side from one end toward a portion in the proximity of a substantially central portion whereas the width of the bottom portion 11 does not vary from the portion in the proximity of the substantially central portion toward the other end.

Figure 13:
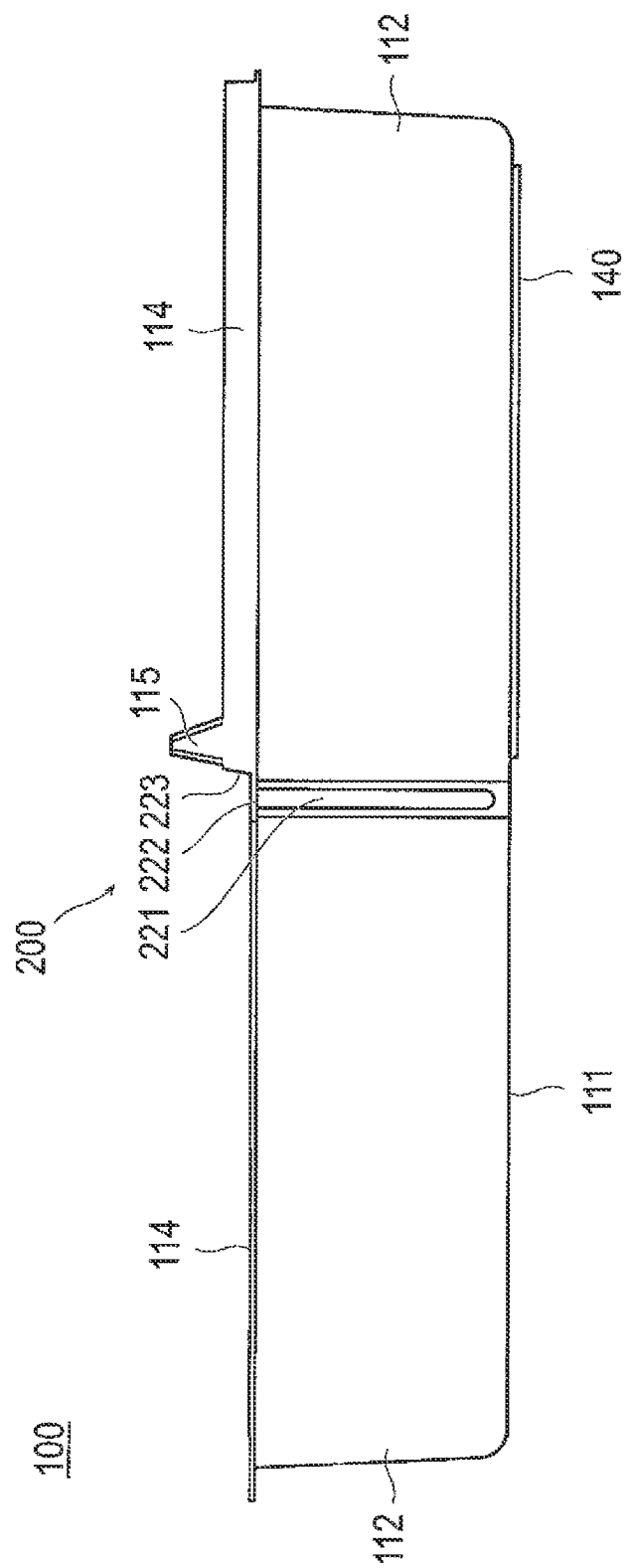
FIG. 13 is a side elevational view showing a modification to the medical tray according to the embodiment.

The side wall deformation guide portion may include, in place of the side wall upper end recessed portion 23, for example, a side wall upper end stepped portion 223 in which the upper end of the side wall 112 is formed in a stepped state (i.e., is step-shaped) toward a bottom portion 111 as shown in FIG. 13.

Further, the side wall 12 or 112 may be swollen to the outer side from the accommodating space S in the proximity of the bottom portion 11 or 111 so as to form an undercut portion. By providing the undercut portion on the side wall 12 or 112, when an elongated and elastic medical instrument such as a catheter 63 or a guide wire is wound and accommodated into the accommodating space S, the medical instrument can be prevented from jumping out by the elastic force.

The detailed description above describes features and aspects of embodiments of a medical tray. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A foldable medical tray sterilized for medical use comprising:
    a bottom portion possessing an outer periphery;
    an upstanding side wall disposed along the outer periphery of the bottom portion and generally perpendicular thereto, the upstanding side wall surrounding an inside of the medical tray sized to hold medical devices, the bottom portion possessing a first surface facing the inside and an oppositely facing second surface;
    the bottom portion and the upstanding side wall being sterilized for medical use;
    the bottom portion and the upstanding side wall being foldable into a foldable condition to reduce a size of the medical tray;
    the upstanding side wall having opposed constricted portions positioned on opposite sides of the inside in opposing relation to one another, the bottom portion possessing a width at the opposed constricted portions, as measured between inner surfaces of the upstanding side wall at the opposing constricted portions, which is narrower than the width of the bottom portion, as measured between inner surfaces of the upstanding side wall, at places on either side of the opposed constricted portions in a lengthwise dimension of the bottom portion; and
    the opposed constricted portions of the upstanding side wall being positioned so that a straight line connecting the opposed constricted portions divides the bottom portion into two parts of unequal size so as to define a first bottom portion part and a second bottom portion part, the first bottom portion part being smaller than the second bottom portion part;
    wherein said second bottom portion part is configured to accommodate said first bottom portion part therein when the medical tray is folded into the foldable condition such that a portion of the upstanding side wall of the first bottom portion part is adjacent to a portion of the upstanding side wall of the second bottom portion part.

2. The medical tray according to claim 1, further comprising an outwardly extending flange positioned at an upper end of the side wall, the outwardly extending flange extending around the entirety of the side wall, except the opposed constricted portions.

3. The medical tray according to claim 2, wherein the opposing portions of the side wall also include at least one of: a side wall grooved portion extending from an upper end of the side wall toward the bottom portion and comprised of a portion of the side wall being recessed toward the inside; a side wall upper end recessed portion in which an upper end of the side wall is recessed toward the bottom portion or a side wall upper end stepped portion in which an upper end of the side wall is step-shaped toward the bottom portion; and a flange groove portion in which an inwardly directed recess is provided in the outwardly extending flange and is inwardly recessed toward the inside.

4. The medical tray according to claim 1, further comprising a folding guiding portion on the bottom portion, the folding guiding portion extending between the opposing portions of the side wall to help guide folding of the bottom portion.

5. The medical tray according to claim 4, wherein the folding guiding portion includes at least one of: a rib or a notch on the bottom portion extending between the opposing positions of the side wall: a bottom edge recessed portion at an edge of the bottom portion that is recessed inwardly; and a bottom edge stepped portion at an edge of the bottom portion that is stepped inwardly.

6. The medical tray according to claim 1, wherein the bottom possesses a length greater than its width, the upstanding side wall including two opposing parts at opposite ends of the upstanding side wall relative to a lengthwise extent, one of the two opposing parts being positioned inside the other opposing part when the medical tray is folded.

7. The medical tray according to claim 1, wherein the first bottom portion part possesses rounded corners and the second bottom portion part possesses corners that are differently configured compared to the rounded corners of the first bottom portion part.

8. The medical tray according to claim 1, wherein the two parts of the bottom portion that are of unequal size are a first bottom portion part and a second bottom portion part, further comprising an elongated tape adhesively attached to the second surface of the second bottom portion part of the bottom portion, a portion of the tape being separable from the second surface of the second bottom portion part of the bottom portion and being adherable to the second surface of the second bottom portion part of the bottom portion to keep the medical tray in the folded condition.

9. A medical tray comprising:
a bottom portion;
a side wall disposed along an outer periphery of the bottom portion and surrounding an accommodating space which accommodates medical devices, the side wall possessing an inner side facing toward the accommodating space, the side wall also possessing an upper end;
a laterally outwardly directed flange at the upper end of the side wall; and
a pair of side wall deformation guiding portions at opposing positions of the side wall to guide the side wall inwardly and downwardly toward the bottom portion when the side wall is deformed into a convex state during folding of the medical tray into a folded condition; and
each of the side wall deformation guiding portions including a side wall groove portion formed in the side wall and recessed toward the inner side of the side wall, each side wall groove portion extending from the upper end of the side wall toward the bottom portion.

10. The medical tray according to claim 9, wherein each of the side wall deformation guiding portions includes at least one of: a constricted portion at which a width of the bottom portion measured between an inner surface of the side wall decreases; a side wall grooved portion extending from an upper end of the side wall toward the bottom portion and comprised of a portion of the side wall being recessed to the inner side of the side wall; a side wall upper end recessed portion in which an upper end of the side wall is recessed toward the bottom portion or a side wall upper end stepped portion in which an upper end of the side wall is step-shaped toward the bottom portion; and a flange groove portion in which an inwardly directed recess is provided in a laterally outwardly extending flange and is inwardly recessed toward an inner side surrounded by the side wall.

11. The medical tray according to claim 10, further comprising a folding guiding portion on the bottom portion, the folding guiding portion extending between the side wall deformation guiding portions at opposing positions of the side wall to guide folding of the bottom portion.

12. The medical tray according to claim 11, wherein the folding guiding portion includes at least one of: a rib or a notch on the bottom portion extending between the side wall deformation guiding portions at opposing positions of the side wall: a bottom edge recessed portion at an edge of the bottom portion that is recessed inwardly; and a bottom edge stepped portion at an edge of the bottom portion that is stepped inwardly.

13. The medical tray according to claim 12, wherein opposing facing portions of the side wall are generally perpendicular to the bottom portion such that, when the bottom portion is folded, one of two opposing facing portions of the side wall which oppose each other is positioned inside the other opposing facing portion.

14. The medical tray according to claim 13, wherein the bottom portion is divided into two portions by a line interconnecting the side wall deformation guiding portions at opposing positions of the side wall so that a first part of the bottom portion is positioned on one side of the line and a second remaining part of the bottom portion is positioned on an opposite side of the line, the first portion of the bottom portion being sized smaller than the second remaining part such that the first part is accommodated inside the second part when the bottom portion is folded.

15. The medical tray according to claim 13, wherein the bottom portion is divided into two portions by a line interconnecting the side wall deformation guiding portions at opposing positions of the side wall so that a first part of the bottom portion is positioned on one side of the line and a second remaining part of the bottom portion is positioned on an opposite side of the line, the first part of the bottom portion possesses rounded corners and the second remaining part possesses corners that are differently configured compared to the rounded corners of the first part.

16. The medical tray according to claim 9, further comprising a folding keeping portion for keeping the medical tray in the folded condition.

17. The medical tray according to claim 9, further comprising a folding guiding portion on the bottom portion, the folding guiding portion extending between the side wall deformation guiding portions at opposing positions of the side wall to guide folding of the bottom portion.

18. The medical tray according to claim 17, wherein the folding guiding portion includes at least one of: a rib or a notch on the bottom portion extending between the side wall deformation guiding portions at opposing positions of the side wall: a bottom edge recessed portion at an edge of the bottom portion that is recessed inwardly; and a bottom edge stepped portion at an edge of the bottom portion that is stepped inwardly.

* * * * *